United States Patent [19]

Drewes et al.

[11] Patent Number: 5,167,693
[45] Date of Patent: Dec. 1, 1992

[54] HERBICIDAL SUBSTITUTED AZINES

[75] Inventors: Mark W. Drewes, Langenfeld; Rolf Kirsten, Monheim; Wolfgang Krämer, Burscheid; Bernd W. Krüger, Gladbach; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 704,545

[22] Filed: May 23, 1991

[30] Foreign Application Priority Data

May 30, 1990 [DE] Fed. Rep. of Germany ....... 4017339
Nov. 21, 1990 [DE] Fed. Rep. of Germany ....... 4037003

[51] Int. Cl.$^5$ ................. C07D 239/60; C07D 401/14; C07D 401/12; A01N 43/54
[52] U.S. Cl. .............................. 71/92; 71/90; 71/86; 544/243; 544/300; 544/301; 544/296; 544/295; 544/310; 544/311; 544/312; 544/313; 544/314; 544/302; 544/317; 544/318; 544/122; 544/123
[58] Field of Search ............... 71/92, 90, 86; 544/243, 544/300, 301, 296, 295, 310, 311, 312, 302, 122

[56] References Cited

U.S. PATENT DOCUMENTS

| 4,808,591 | 2/1989 | Santini | 514/274 |
|---|---|---|---|
| 4,859,679 | 8/1989 | Santini | 514/273 |
| 5,015,285 | 5/1991 | Rheinheimer et al. | 544/299 |
| 5,053,070 | 10/1991 | Gohbara et al. | 71/92 |
| 5,057,143 | 10/1991 | Rheinhimer et al. | 71/91 |
| 5,085,686 | 2/1992 | Vogelbacher et al. | 71/91 |
| 5,100,458 | 3/1992 | Eicken et al. | 71/92 |

FOREIGN PATENT DOCUMENTS

| 0334137 | 9/1989 | European Pat. Off. . |
|---|---|---|
| 0346789 | 12/1989 | European Pat. Off. . |
| 0350691 | 1/1990 | European Pat. Off. . |
| 0363040 | 4/1990 | European Pat. Off. . |
| 0363818 | 7/1990 | European Pat. Off. . |

Primary Examiner—John M. Ford
Attorney, Agent, or Firm—Sprung Horn Kramer & Woods

[57] ABSTRACT

Herbicidal substituted azines of the formula

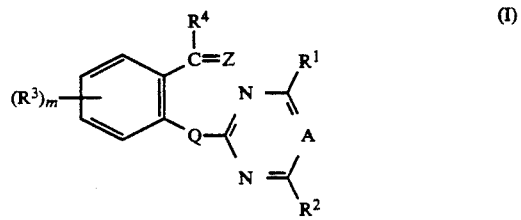

in which
m represents the numbers 0, 1, 2 or 3,
A represents nitrogen or a C-X group where X represents hydrogen or halogen,
Q represents oxygen or sulphur,
$R^1$ and $R^2$ are identical or different and represent hydrogen, halogen, alkyl, halogenoalkyl, alkoxyalkyl, alkoxy, halogenoalkoxy, alkylthio, alkylamino or dialkylamino,
$R^3$ represents amino, hydroxyl, halogen, alkyl, halogenoalkyl, alkoxy, halogenoalkoxy, alkylamino, dialkylamino, alkylcarbonylamino, alkoxycarbonyl-amino or alkylsulphonylamino,
$R^4$ represents hydrogen or alkyl and
Z represents
$N$-$R^5$ or

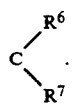

8 Claims, No Drawings

HERBICIDAL SUBSTITUTED AZINES

The invention relates to new substituted azines, to a process and to new intermediates for their preparation, and to their use as herbicides.

A series of substituted azines having herbicidal properties has already been disclosed (compare JP-A 54117486 - cit. in Chem. Abstracts 93, 150268c; EP-A 223,406; EP-A 249,708; JP-A 63258467 - cit. in Chem. Abstracts 110, 130532a; JP-A 63258463 - cit. in Chem. Abstracts 110, 192853q; EP-A 287,079; EP-A 374,839). However, compounds from the publications mentioned have not gained considerable importance to date.

The new substituted azines of the general formula (I) have now been found,

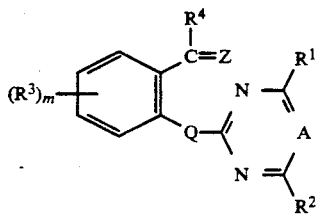

in which
m represents the numbers 0, 1, 2 or 3,
A represents nitrogen or a C-X group where X represents hydrogen or halogen,
Q represents oxygen or sulphur,
$R^1$ and $R^2$ are identical or different and represent hydrogen, halogen, alkyl, halogenoalkyl, alkoxyalkyl, alkoxy, halogenoalkoxy, alkylthio, alkylamino or dialkylamino,
$R^3$ represents amino, hydroxyl, halogen, alkyl, halogenoalkyl, alkoxy, halogenoalkoxy, alkylamino, dialkylamino, alkylcarbonylamino, alkoxycarbonylamino or alkylsulphonylamino,
$R^4$ represents hydrogen or alkyl and
Z represents one of the groups below:
N-$R^5$ or

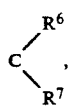

where
$R^5$ represents hydrogen, amino, or in each case optionally substituted alkyl, alkenyl, alkynyl, aralkyl, aryl, alkoxycarbonyloxy, arylaminocarbonyloxy, carboxyalkoxy, alkoxycarbonylalkoxy, alkylamino, dialkylamino, aralkylamino, arylamino, N-alkyl-N-arylamino, alkylcarbonylamino, arylcarbonylamino, heteroarylamino, heteroarylcarbonylamino, alkoxycarbonylamino, alkylsulphonylamino or arylsulphonylamino,
$R^6$ represents hydrogen, halogen, cyano, carboxyl, alkoxycarbonyl, alkylcarbonylamino or dialkoxyphosphoryl and
$R^7$ represents formyl, cyano, carboxyl, hydroxymethyl, carbamoyl, or in each case optionally substituted alkoxycarbonyl, cycloalkoxycarbonyl, aralkoxycarbonyl, aryloxycarbonyl, heterocyclylalkoxycarbonyl, alkylthiocarbonyl, aralkylthiocarbonyl, arylthiocarbonyl, alkylaminocarbonyl, cycloalkylaminocarbonyl, aralkylaminocarbonyl, arylaminocarbonyl, dialkylaminocarbonyl, alkylhydrazinocarbonyl, arylhydrazinocarbonyl, pyrrolidinylcarbonyl,- piperidinylcarbonyl, morpholinylcarbonyl, piperazinylcarbonyl, phthalimidoxycarbonyl, or represents the group

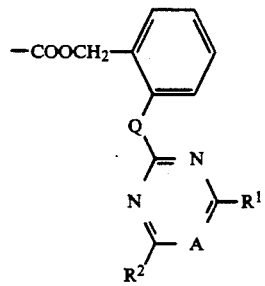

in which A, Q, $R^1$ and $R^2$ have the meanings given above, or together with $R^6$ represents the group —CO—O—$(CH_2)_n$— where n represents the numbers 1 to 4.

The new substituted azines of the general formula (I) are obtained when corresponding carbonyl compounds of the general formula (II)

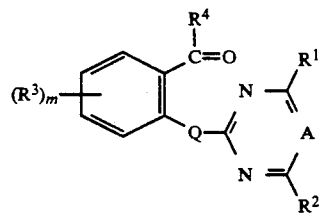

in which
m, A, Q, $R^1$, $R^2$, $R^3$ and $R^4$ have the meaningsgiven above,
are reacted with amino or methylene compounds of the general formula (II)

$$H_2Z \qquad (III)$$

in which
Z has the meaning given above,
if appropriate in the presence of a reaction auxiliary and if appropriate in the presence of a diluent, and, if appropriate, the products obtained in this process are subsequently converted into other derivatives according to the definition of the compounds of the formula (I) using customary methods.

The new substituted azines of the general formula (I) are distinguished by a powerful herbicidal action.

The invention preferably relates to compounds of the formula (I) in which
m represents the numbers 0, 1, or 2,
A represents nitrogen or a C-X group where X represents hydrogen or halogen,
Q represents oxygen or sulphur,
$R^1$ and $R^2$ are identical or different and represent hydrogen, halogen, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogeno alkoxy, $C_1$-$C_4$-alkylthio, $C_1$-$C_4$-alkylamino or di-($C_1$-$C_2$-alkyl)-amino, $R^3$ represents amino, hydroxyl, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylamino, di-($C_1$–$C_2$-alkyl)-amino, $C_1$–$C_4$-alkyl-carbonylamino, $C_1$–$C_4$-alkoxy-carbonylamino or $C_1$–$C_4$-alkylsulphonylamino, $R^4$ represents hydrogen or $C_1$–$C_4$-alkyl and Z represents one of the groups below:

N-$R^5$ or

where $R^5$ represents hydrogen, amino or represents $C_1$–$C_6$-alkyl, $C_3$–$C_6$-alkenyl, $C_3$–$C_6$-alkinyl, carboxy-$C_1$–$C_2$-alkoxy, $C_1$–$C_6$-alkoxycarbonyloxy, $C_1$–$C_4$-alkoxycarbonyl-$C_1$–$C_2$-alkoxy, $C_1$–$C_6$-alkylamino, di-($C_1$–$C_2$-alkyl)-amino, $C_1$–$C_6$-alkyl-carbonylamino, $C_1$–$C_6$-alkoxy-carbonylamino or $C_1$–$C_6$-alkyl-sulphonylamino, each of which is optionally substituted by halogen, or represents phenyl, phenyl-$C_1$–$C_4$-alkyl, phenylaminocarbonyloxy, phenylamino, phenyl-$C_1$–$C_4$-alkylamino, N-($C_1$–$C_4$-alkyl)-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, hydroxyl, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, C $C_1$–$C_4$-alkoxycarbonyl and/or di-($C_1$–$C_2$-alkyl)-amino, $R^6$ represents hydrogen, halogen, cyano, carboxyl, $C_1$–$C_6$-alkoxy-carbonyl, $C_1$–$C_6$-alkylcarbonylamino or di-($C_1$–$C_4$-alkoxy)-phosphoryl, and $R^7$ represents formyl, cyano, carboxyl, hydroxymethyl or carbamoyl, or represents $C_1$–$C_6$-alkoxy-carbonyl, $C_5$–$C_6$-cycloalkyloxy-carbonyl, $C_1$–$C_6$-alkylthiocarbonyl, $C_1$–$C_6$-alkylamino-carbonyl or $C_5$–$C_6$-cycloalkylamino-carbonyl, each of which is optionally substituted by halogen, carboxyl or $C_1$–$C_4$-alkoxycarbonyl, or represents di-($C_1$–$C_2$-alkyl)-aminocarbonyl, or $C_1$–$C_4$-alkylamino-carbonyl-$C_1$–$C_4$-alkoxycarbonyl, or di-($C_1$–$C_2$-alkyl)-aminocarbonyl-$C_1$–$C_4$-alkoxy-carbonyl, or phenylaminocarbonyl-$C_1$–$C_4$-alkoxy-carbonyl, or N-methyl-phenylaminocarbonyl-$C_1$–$C_4$-alkoxy-carbonyl, or represents pyrrolidinylcarbonyl, piperidinylcarbonyl, morpholinylcarbonyl or piperazinylcarbonyl, each of which is optionally substituted by methyl and/or ethyl, or represents phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthiocarbonyl, phenylaminocarbonyl, phenyl-$C_1$–$C_4$-alkylaminocarbonyl, N-($C_1$–$C_4$-alkyl)-phenylamino-carbonyl or phenylhydrazinocarbonyl, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)-amino, or represents phthalimidoxycarbonyl, or represents the group

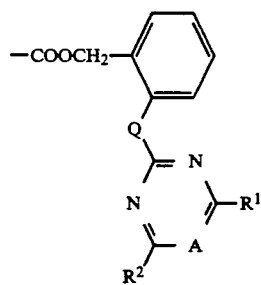

in which A, Q, $R^1$ and $R^2$ have the meanings given above as being preferred, or together with $R^6$ represents the group —CO—O—$(CH_2)_n$— where n represents the numbers 2 or 3.

The aliphatic hydrocarbon radicals listed in the definition of the compounds according to the invention (for example alkyl, alkenyl, alkynyl) are in each case straight-chain or branched, also in combination with heteroatoms (for example in alkoxy, alkylthio, alkylamino).

Halogen in each case generally represents fluorine, chlorine, bromine or iodine, preferably fluorine, chlorine or bromine, in particular fluorine or chlorine.

In particular, the invention relates to compounds of the formula (I), in which m represents the numbers 0, 1, or 2, A represents nitrogen or a CH group, Q represents oxygen, $R^1$ represents hydrogen, chlorine, methyl, ethyl, trifluoromethyl, methoxymethyl, methoxy, ethoxy, difluoromethoxy, methylthio, methylamino, ethylamino or dimethylamino, $R^2$ represents hydrogen, chlorine, methyl, ethyl, trifluoromethyl, methoxy, ethoxy, difluoromethoxy, methylthio, methylamino, ethylamino or dimethylamino, $R^3$ represents amino, hydroxyl, fluorine, chlorine, bromine, methyl, ethyl, trifluoromethyl, methoxy, difluoromethoxy, trifluoromethoxy, methylamino, dimethylamino, acetylamino, methoxycarbonylamino or methylsulphonylamino, $R^4$ represents hydrogen or methyl and Z represents one of the groups below:

N-$R^5$ or

where $R^5$ represents hydrogen, amino, or methyl, ethyl, propyl, isopropyl, butyl, isobutyl, sec-butyl, tert-butyl, allyl, propargyl, carboxymethoxy, carboxyethoxy, methoxycarbonyloxy, ethoxycarbonyloxy, propoxycarbonyloxy, butoxycarbonyloxy, methoxycarbonylmethoxy, ethoxycarbonylmethoxy, methoxycarbonylethoxy, ethoxycarbonylethoxy, methylamino, ethylamino, propylamino, isopropylamino, butylamino, isobutylamino, secbutylamino, tert-butylamino, dimethylamino, acetylamino, propionylamino, methoxycarbonylamino, ethoxycarbonylamino, methylsulphonylamino or ethylsulphonylamino or represents phenyl, benzyl, phenylaminocarbonyloxy, phenylamino, benzylamino, N-methyl-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, hydroxyl, cyano, fluorine, chlorine, bromine, methyl, trifluoromethyl, methoxy, trifluoromethoxy, methylthio or trifluoromethylthio, $R^6$ represents hydrogen, fluorine, chlorine, cyano, carboxyl, $C_1$-$C_4$-alkoxy-carbonyl, $C_1$-$C_4$-alkylcarbonylamino, dimethoxyphosphoryl or diethoxyphosphoryl, and $R^7$ represents formyl, cyano, carboxyl, hydroxymethyl or carbamoyl, or represents $C_1$-$C_4$-alkoxy-carbonyl, $C_5$-$C_6$-cycloalkyloxy-carbonyl, $C_1$-$C_4$-alkylthiocarbonyl, $C_1$-$C_4$-alkylamino-carbonyl or $C_5$-$C_6$-cycloalkylaminocarbonyl, each of which is optionally substituted by fluorine, chlorine, carboxyl or $C_1$-$C_4$-alkoxycarbonyl, or represents dimethylaminocarbonyl, or $C_1$-$C_4$-alkylaminocarbonyl-$C_1$-$C_4$-alkoxycarbonyl, or dimethylaminocarbonyl-$C_1$-$C_4$-alkoxy-carbonyl, or N-methylphenylaminocarbonyl-$C_1$-$C_4$-alkoxy-carbonyl, or represents pyrrolidinyl-carbonyl, piperidinylcarbonyl, morpholinyl-carbonyl or piperazinylcarbonyl, each of which is optionally substituted by methyl and/or ethyl, or represents phenoxycarbonyl, benzyloxycarbonyl, phenylthiocarbonyl, benzylthiocarbonyl, phenylaminocarbonyl, benzylaminocarbonyl, N-methyl-phenylaminocarbonyl or phenylhydrazinocarbonyl, each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or represents the group

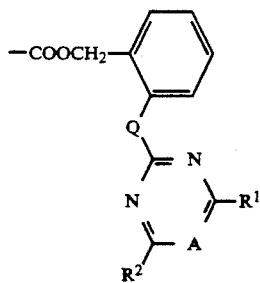

in which A, Q, $R^1$ and $R^2$ have the meanings given above as being particularly preferred, or together with $R^6$ represents the group —CO—O—CH$_2$CH$_2$—.

Very particularly preferred compounds of the formula (I) are those in which m represents the numbers 0, 1 or 2, A represents a CH group, Q represents oxygen, $R^1$ represents methoxy, $R^2$ represents methoxy, $R^3$ represents fluorine, chlorine or methyl, $R^4$ represents hydrogen and Z has the meaning given above as being particularly preferred.

If, for example, 2-(4,6-dimethoxy-pyrimidin-2-yl-oxy)benzaldehyde and acetohydrazide are used as starting substances in the process for the preparation of the compounds of the formula (I) according to the invention, the course of the reaction can be outlined by the following equation:

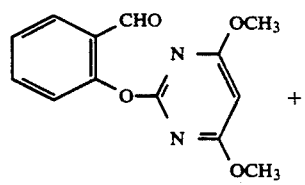

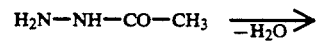

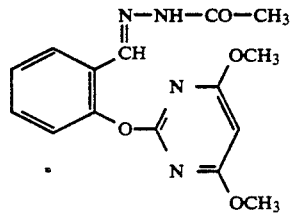

Formula (II) provides a general definition of the carbonyl compounds to be used as starting substances in the process for the preparation of compounds of the formula (I) according to the invention.

In formula (II), A, Q, $R^1$, $R^2$, $R^3$ and $R^4$ preferably, or in particular, have the meanings which have already been given above in connection with the description of the compounds of the formula (I) according to the invention as being preferred, or as particularly preferred, for A, Q, $R^1$, $R^2$, $R^3$ and $R^4$.

Examples of the starting substances of the formula (II) which may be mentioned are:

2-(4,6-dimethyl-pyrimidin-2-yl-oxy)-,
2-(4-methoxy-6-methyl-pyrimidin-2-yl-oxy)-,
2-(4,6-dimethoxy-pyrimidin-2-yl-oxy)-,
2-(4-methoxy-6-trifluoromethyl-pyrimidin-2-yl-oxy)-,
2-(4,6-dimethyl-s-triazin-2-yl-oxy)-,
2-(4-methoxy-6-methyl-s-triazin-2-yl-oxy)- and
2-(4,6-dimethoxy-s-triazin-2-yl-oxy)-benzaldehyde.

The starting substances of the formula (II) are known and/or can be prepared by processes known per se (compare EP-A 223,406; EP-A 249,708; JP-A 63258467 - cit. in Chem. Abstracts 110, 130532a; JP-A 63258463 - cit. in Chem. Abstracts 110, 192853q; EP-A 287,079).

The starting substances of the general formula (IIa)

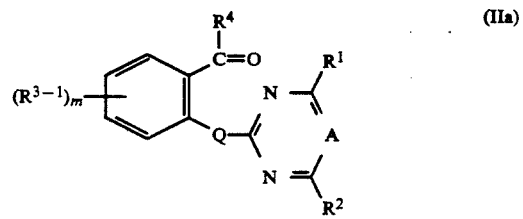

in which

A, Q, R¹, R² and R⁴ have the meanings given above,
m represents the numbers 1 or 2 and
R³⁻¹ represents fluorine and, if appropriate, additionally chlorine,
are new and subject-matter of the present application.

In formula (IIa), A, Q, R¹, R² and R⁴ preferably, or in particular, have those meanings which have already been given above in connection with the description of the compounds of the formula (I) according to the invention as being preferred, or as particularly preferred, for A, Q, R¹, R² and R⁴; m preferably represents the numbers 1 or 2 and R³⁻¹ preferably represents fluorine.

The new compounds of the formula (IIa) are obtained when halogen compounds of the general formula (IV)

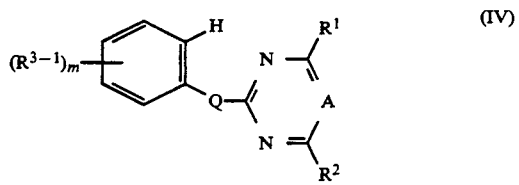  (IV)

in which
m, A, Q, R¹, R² and R³⁻¹ have the meaning given above in formula (IIa),
are treated with a metallating agent such as, for example, butyllithium, in the presence of an inert diluent such as, for example, tetrahydrofuran, at temperatures between −20° C. and −120° C., preferably between −50° C. and −80° C., the product is subsequently reacted in situ with carboxamides of the general formula (V)

R⁴—CO—NR₂    (V)

in which
R⁴ has the meaning given above and
R represents alkyl,
at temperatures between 0° C. and −80° C., and the product is worked up by customary methods (cf. the preparation examples).

In formula (IV), A, Q, R¹ and R² preferably, or in particular, have those meanings which have already been given above in connection with the description of the compounds of the formula (I) according to the invention as being preferred, or as particularly preferred, for A, Q, R¹ and ²R; m preferably represents the numbers 1 or 2 and R³⁻¹ preferably represents fluorine.

The halogen compounds of the formula (IV) were hitherto not known from the literature and are likewise subject-matter of the present application.

The new compounds of the formula (IV) are obtained when halogenated (thio)phenols of the formula (VI)

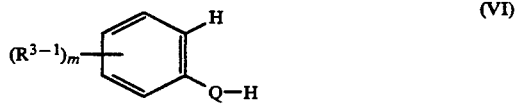  (VI)

in which
m, Q and R³⁻¹ have the meanings given above,
are reacted with reactive azines of the formula (VII)

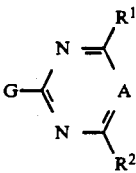  (VII)

in which
A, R¹ and R² have the meanings given above and
G represents a nucleofugic leaving group,
if appropriate in the presence of an acid acceptor such as potassium carbonate, and if appropriate in the presence of a diluent such as, for example, acetonitrile, at temperatures between 20° C. and 120° C. (cf. the preparation examples).

In formula (VI), m preferably represents the numbers 1 or 2, Q preferably represents oxygen and R³⁻¹ preferably represents fluorine.

The halogenated (thio)phenols of the formula (VI) are known chemicals for synthesis.

In formula (VII), A, R¹ and R² preferably, or in particular, have those meanings which have already been given above in connection with the description of the compounds of the formula (I) according to the invention as being preferred, or as particularly preferred, for A, R¹ and R²; G preferably represents chlorine or methylsulphonyl.

The reactive azines of the formula (VII) are known and/or can be prepared by processes known per se (cf. J. Chem. Soc. 1957, 1830, 1833; J. Org. Chem. 26 (1961), 792; U.S. Pat. No. 3,308,119; U.S. Pat. No. 4,711,959).

In formula (V), R⁴ preferably, or in particular, has those meanings which have already been given above in connection with the description of the compounds of the formula (I) according to the invention as being preferred, or as particularly preferred, for R⁴; R preferably represents C₁-C₄-alkyl, in particular methyl.

The carboxamides of the formula (V) are known chemicals for synthesis.

Formula (III) provides a general definition of the amino or methylene compounds furthermore to be used as starting substances in the process according to the invention for the preparation of compounds of the formula (I).

In formula (III), Z preferably, or in particular, has those meanings which have already been given above in connection with the description of the compounds of the formula (I) according to the invention as being preferred, or as particularly preferred, for Z.

Examples of the starting substances of the formula (III) which may be mentioned are: ammonia, hydroxylamine, hydrazine, methylamine, ethylamine, propylamine, isopropylamine, butylamine, isobutylamine, sec-butylamine, tert-butylamine, allylamine, propargylamine, O-methyl-, O-ethyl-, O-propyl-, O-isopropyl-, O-butyl-, O-isobutyl- and O-sec-butyl-hydroxylamine, O-allyl-hydroxylamine, methyl aminooxyacetate and ethyl aminooxyacetate, methyl α-aminooxy-propionate and ethyl α-aminooxypropionate, methylhydrazine, ethylhydrazine, propylhydrazine, isopropylhydrazine, butylhydrazine, isobutylhydrazine, sec-butyl-hydrazine, tert-butylhydrazine, N,N-dimethylhydrazine, acetohydrazide, propionylhydrazide, methoxycarbonylhydrazine, ethoxycarbonylhydrazine, methylsulphonylhydrazine, ethylsulphonylhydrazine, phenylhydrazine, benzoylhydrazine, benzenesulphonyl hydrazide, p-toluenesulphonyl hydrazide, malonic acid, cyanoacetic acid, malononitrile, methyl cyanoacetate and ethyl cyanoacetate, dimethyl malonate and diethyl malonate, and γ-butyrolactone.

The starting substances of the formula (III) are known chemicals for synthesis.

The process according to the invention for the preparation of the new substituted azines of the formula (I) is preferably carried out using diluents. Suitable diluents besides water are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

If appropriate, the process according to the invention is carried out in the presence of a reaction auxiliary. Suitable reaction auxiliaries are substances which are customarily used for controlling and/or accelerating condensation reactions between carbonyl compounds and amino or methylene compounds. These include, in particular, nitrogen compounds such as, for example, ammonium acetate, β-alanine, pyridine and piperidine.

In the process according to the invention, the reaction temperatures can be varied within a substantial range. In general, the reaction is carried out at temperatures between 0° C. and 150° C., preferably at temperatures between 10° C. and 120° C.

In general, the process according to the invention is carried out under atmospheric pressure. However, it is also possible to carry out the process under increased or reduced pressure.

For carrying out the process according to the invention, the starting substances required in each case are generally employed in approximately equimolar amounts. However, it is also possible to use one of the two components employed in each case in a larger excess. In general, the reactions are carried out in a suitable diluent, if appropriate in the presence of a reaction auxiliary, and the reaction mixture is stirred for several hours at the particular temperature required. Working-up in the process according to the invention is carried out in each case by customary methods (compare the preparation examples).

The active compounds according to the invention can be used as defoliants, desiccants, agents for destroying broad-leaved plants and, in particular, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum and Mercurialis.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture lands and for the selective combating of weeds in annual cultures.

The compounds of the formula (I) according to the invention can be employed both pre-emergence and post-emergence methods for combating monocotyledon and dicotyledon weeds.

To a certain extent, the compounds according to the invention also show a fungicidal action, for example against Pyricularia oryzae.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are prepared in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methyl-cellulose.

Adhesives such as carboxymethylcellulose, natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N,-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxy- propionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide(ALACHLOR);2-chloro-4-ethylamino-6-isopropylamino-1,3,5-triazine (ATRAZINE); methyl 2[[[[[(4,6-dimethoxypyrimidin-2-yl)-amino]-carbonyl]-amino]sulphonyl]-methyl]-benzoate(- BENSULFURON); 3-isopropyl-2,1,3-benzothiadiazin-4-one 2,2-dioxide (BENTAZONE); methyl 5-(2,4-dichlorophenoxy)-2-nitrobenzoate(BIFENOX); 3,5-dibromo-4-hydroxy-benzonitrile; (BROMOXYNIL); ethyl 2-{[(4-chloro-6-methoxy-2-pyrimidinyl)-aminocarbonyl]-aminosulphonyl}-benzoate (CHLORIMURON); N,N-dimethyl-N'-(3-chloro-4-methylphenyl)-urea (CHLORTOLURON); 2-chloro-4-ethylamino-6-(3-cyanopropylamino)-1,3,5-triazi (CYANAZINE); 4-amino-6-t-butyl-3-ethylthio-1,2,4-triazin-5(4H)-one (ETHIOZIN); 2-{4-[(6-chloro-2-benzoxazolyl)oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); 5-(2-chloro-4-trifluoromethylphenoxy)-N-methylsulphonyl-2-nitrobenzamide (FOMESAFEN); N-phosphonomethyl-glycine (GLYPHOSATE); 2-{4-[(3-chloro-5-(trifluoromethyl)-2-pyridinyl)-oxy]-phenoxy}-propanoic acid or its ethyl ester (HALOXYFOP); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); 2-[1-(ethoxamino)-butylidene] -5-(2-ethylthiopropyl)-1,3-cyclohexadione (SETHOXYDIM); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON) and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

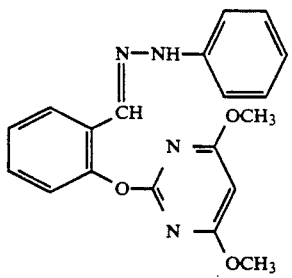

A mixture of 2.7 g (10 mmol) of 2-(4,6-dimethoxypyrimidin-2-yl-oxy)-benzaldehyde, 1.1 g (10 mmol) phenylhydrazine and 40 ml of toluene is stirred for 2 hours at 20° C. and subsequently concentrated. The residue is brought to crystallization with ethanol/water (1:1), and the crystallized product is isolated by filtration with suction.

2.6 g (75% of theory) of 2-(4,6-dimethoxy-pyrimidin-2-yl-oxy)-benzaldehyde phenylhydrazone of melting point are obtained.

Example 2

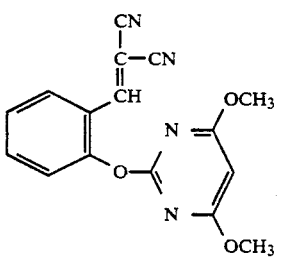

A mixture of 2.6 g (10 mmol) of 2-(4,6-dimethoxypyrimidin-2-yl-oxy)-benzaldehyde, 0.67 g (10 mmol) malononitrile, 0.1 g of ammonium acetate and 80 ml of toluene is heated to the boil for 5 hours on a water separator. The mixture is subsequently concentrated, and the residue is brought to crystallization with diethyl ether/petroleum ether. The crystalline product is isolated by filtration with suction.

2.2 g (71% of theory) of α-(2-(4,6-dimethoxy-pyrimidin-2-yl-oxy)-phenyl)-methylene-malononitrile of melting point 123° C. are obtained.

Examples of other compounds of the formula (I) which can be prepared analogously to Examples 1 or 2 and following the general description of the preparation process according to the invention or by subsequent reactions following customary methods are those listed in Table 1 below.

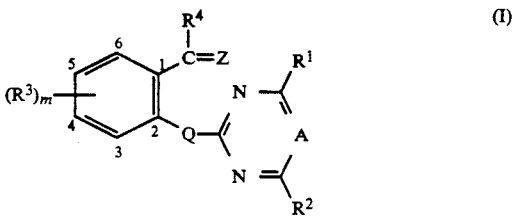

(I)

(Q is bonded always in the 2-position).

TABLE 1

| Example No. | A | Q | R¹ | R² | R³ | R⁴ | m | Z | Melting Point (°C.) |
|---|---|---|---|---|---|---|---|---|---|
| | | (2-Position) | | | | | | | |
| 3 | CH | O | OCH₃ | OCH₃ | — | H | 0 | CHCOOC₂H₅ | 70 |
| 4 | N | O | OCH₃ | OCH₃ | — | H | 0 | CHCOOH | 196 |
| 5 | N | O | OCH₃ | OCH₃ | — | H | 0 | CHCOOC₂H₅ | 128 |
| 6 | CH | O | OCH₃ | OCH₃ | — | H | 0 | CHCH₂OH | (amorphous) |
| 7 | CH | O | OCH₃ | OCH₃ | — | H | 0 | (lactone structure) | 124 |
| 8 | CH | O | OCH₃ | OCH₃ | — | H | 0 | CHCNHNH-(2-CF₃-phenyl), C=O | 147 |
| 9 | CH | O | OCH₃ | OCH₃ | (5-)F | H | 1 | (lactone structure) | 126 |

TABLE 1-continued

Examples of the compounds of the formula (I)

| Example No. | A | Q | $R^1$ | $R^2$ | $R^3$ | $R^4$ | m | Z | Melting Point (°C.) |
|---|---|---|---|---|---|---|---|---|---|
| 10 | N | O | $OCH_3$ | $OCH_3$ | (5-)F | H | 1 | 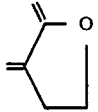 | 139 |
| 11 | CH | O | $OCH_3$ | $OCH_3$ | — | H | 0 | $C(COOC_2H_5)_2$ | (amorphous) |
| 12 | CH | O | $OCH_3$ | $OCH_3$ | (5-)F | H | 1 | CHCOOH | 193 |
| 13 | N | O | $OCH_3$ | $OCH_3$ | — | H | 0 | $CHCH_2OH$ | (amorphous) |
| 14 | CH | O | $OCH_3$ | $OCH_3$ | — | H | 0 | $CHCOOCH(CH_3)_2$ | (amorphous) |
| 15 | CH | O | $OCH_3$ | $OCH_3$ | (5-)$CF_3$ | H | 1 | CHCOOH | (amorphous) |
| 16 | CH | O | $OCH_3$ | $OCH_3$ | — | H | 0 | $\overset{O}{\underset{\|}{CHCNHCH(CH_3)_2}}$ | 131 |
| 17 | CH | O | $OCH_3$ | $OCH_3$ | — | H | 0 |  | 182 |
| 18 | CH | O | $OCH_3$ | $OCH_3$ | — | H | 0 | 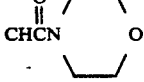 | 153 |
| 19 | CH | O | $OCH_3$ | $OCH_3$ | — | H | 0 | 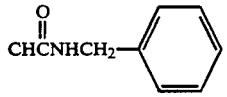 | (amorphous) |
| 20 | CH | O | $OCH_3$ | $OCH_3$ | — | H | 0 | 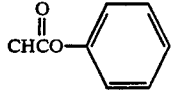 | (amorphous) |
| 21 | CH | O | $OCH_3$ | $OCH_3$ | — | H | 0 | $\overset{O}{\underset{\|}{CHCO(CH_2)_3CH_3}}$ | (amorphous) |
| 22 | CH | O | $OCH_3$ | $OCH_3$ | (4-)F | H | 1 | CHCOOH | 179 |
| 23 | CH | O | $OCH_3$ | $OCH_3$ | (5-)F | H | 1 | $CHCH_2OH$ | (amorphous) |
| 24 | CH | O | $OCH_3$ | $OCH_3$ | (4-)F | H | 1 | $CHCH_2OH$ | (amorphous) |
| 25 | CH | O | $OCH_3$ | $OCH_3$ | (4-)F | H | 1 | $C(COOC_2H_5)_2$ | (amorphous) |
| 26 | CH | O | $OCH_3$ | $OCH_3$ | — | H | 0 | CHCHO | 94 |
| 27 | CH | O | $OCH_3$ | $OCH_3$ | (5-)$CH_3$ | H | 1 | CHCOOH | 162 |
| 28 | CH | O | $OCH_3$ | $OCH_3$ | (5-)Cl | H | 1 | CHCOOH | 200 |
| 29 | CH | O | $OCH_3$ | $OCH_3$ | (5-)Cl | H | 1 | $C(COOC_2H_5)_2$ | (amorphous) |
| 30 | CH | O | $OCH_3$ | $OCH_3$ | (5-)Cl | H | 1 | $CHCH_2OH$ | (amorphous) |
| 31 | CH | O | $OCH_3$ | $OCH_3$ | (5-)$CH_3$ | H | 1 | $CHCH_2OH$ | (amorphous) |
| 32 | CH | O | $CH_3$ | $OCH_3$ | — | H | 0 | $C(COOC_2H_5)_2$ | (amorphous) |
| 33 | CH | O | $OCH_3$ | $OCH_3$ | — | H | 0 | 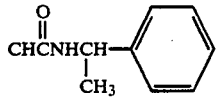 | (amorphous) |
| 34 | CH | O | $OCH_3$ | $OCH_3$ | — | H | 0 | 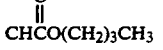 | 123 |
| 35 | CH | O | $OCH_3$ | $OCH_3$ | — | H | 0 | 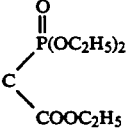 | (amorphous) |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 36 | CH | O | OCH₃ | OCH₃ | — | H | 0 | 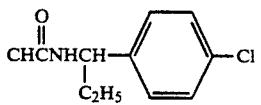 | (amorphous) |
| 37 | CH | O | OCH₃ | OCH₃ | — | H | 0 |  | (amorphous) |
| 38 | CH | O | OCH₃ | OCH₃ | — | H | 0 | 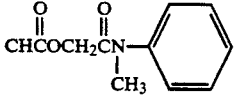 | (amorphous) |
| 39 | CH | O | OCH₃ | OCH₃ | — | H | 0 | CHCN | (amorphous) |
| 40 | CH | O | OCH₃ | OCH₃ | — | H | 0 | 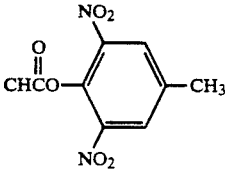 | 175 |
| 41 | CH | O | OCH₃ | OCH₃ | — | H | 0 | 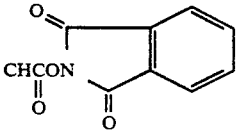 | 85 |
| 42 | CH | O | OCH₃ | OCH₃ | — | H | 0 | 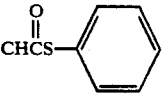 | (amorphous) |
| 43 | CH | O | OCH₃ | OCH₃ | (5-)F | H | 1 | CHCN | (amorphous) |
| 44 | CH | O | OCH₃ | OCH₃ | — | H | 0 | CFCOOC₂H₅ | (amorphous) |
| 45 | CH | O | OCH₃ | OCH₃ | (5-)F | H | 1 | CFCOOC₂H₅ | (amorphous) |
| 46 | CH | O | OCH₃ | OCH₃ | — | H | 0 | 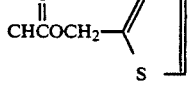 | (amorphous) |
| 47 | CH | O | OCH₃ | OCH₃ | — | H | 0 | 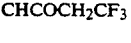 | (amorphous) |
| 48 | CH | O | OCH₃ | OCH₃ | — | H | 0 | 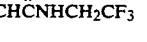 | (amorphous) |
| 49 | CH | O | OCH₃ | OCH₃ | — | H | 0 | 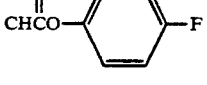 | (amorphous) |
| 50 | CH | O | OCH₃ | OCH₃ | — | H | 0 | 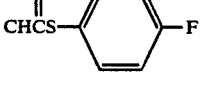 | (amorphous) |
| 51 | CH | O | OCH₃ | OCH₃ | — | H | 0 | 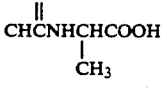 | 104 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 52 | CH | O | OCH₃ | OCH₃ | — | H | 0 | $\underset{\underset{CH_2CH(CH_3)_2}{|}}{CHCNHCHCOOH}$ with C=O | 102 |
| 53 | CH | O | OCH₃ | OCH₃ | — | H | 0 | CHCOCHCOOC₂H₅ with CH₃ branch | (amorphous) |
| 54 | CH | O | OCH₃ | OCH₃ | — | H | 0 | CHCNH-cyclopentyl-COOH | (amorphous) |
| 55 | CH | O | OCH₃ | OCH₃ | — | H | 0 | CHCNH-cyclohexyl-COOH | 238 |
| 56 | CH | O | OCH₃ | OCH₃ | — | H | 0 | CHCOCH₂-(2-{[4,6-dimethoxypyrimidin-2-yl]oxy}phenyl) | 141 |
| 57 | CH | O | OCH₃ | OCH₃ | — | H | 0 | CHCOCH₂-(4-fluoro-2-{[4,6-dimethoxypyrimidin-2-yl]oxy}phenyl) | (amorphous) |
| 58 | CH | O | OCH₃ | OCH₃ | (5-)F | H | 1 | CH=C(CN)(COOC₂H₅) | 119 |
| 59 | CH | O | OCH₃ | OCH₃ | (5-)F | H | 1 | N—NH—C₆H₅ | (amorphous) |
| 60 | CH | O | OCH₃ | OCH₃ | — | H | 0 | N—NH—(2,3,4,5,6-pentafluorophenyl) | 191 |

TABLE 1-continued

Examples of the compounds of the formula (I)

| Example No. | A | Q | $R^1$ | $R^2$ | $R^3$ | $R^4$ | m | Z | Melting Point (°C.) |
|---|---|---|---|---|---|---|---|---|---|
| 61 | CH | O | OCH₃ | OCH₃ | — | H | 0 | N—NH—(2,4-dichlorophenyl) | 200 |
| 62 | CH | O | OCH₃ | OCH₃ | — | H | 0 | N—NH—SO₂—CH₃ | (amorphous) |
| 63 | CH | O | OCH₃ | OCH₃ | — | H | 0 | N—NH—(4-chlorophenyl) | 149 |
| 64 | CH | O | OCH₃ | OCH₃ | — | H | 0 | N—NH—(4-fluorophenyl) | 134 |
| 65 | CH | O | OCH₃ | OCH₃ | — | CH₃ | 0 | N—NH—phenyl | 116 |
| 66 | CH | O | OCH₃ | OCH₃ | — | H | 0 | N—N(CH₃)—phenyl | 82 |
| 67 | CH | O | OCH₃ | OCH₃ | — | H | 0 | CFCOOH | (amorphous) |
| 68 | CH | O | OCH₃ | OCH₃ | — | H | 0 | N—NH—SO₂—(2-chlorophenyl) | 184 |
| 69 | CH | O | OCH₃ | OCH₃ | — | H | 0 | N—NH—SO₂—(2-trifluoromethylphenyl) | 165 |
| 70 | CH | O | OCH₃ | OCH₃ | (5-)F | H | 1 | C(CN)₂ | 172 |
| 71 | C—Br | O | OCH₃ | OCH₃ | — | H | 0 | CHCOOH | 220 |
| 72 | CH | O | OCH₃ | OCH₃ | (6-)F | H | 1 | N—NH—phenyl | (amorphous) |
| 73 | CH | O | OCH₃ | OCH₃ | (6-)F | H | 1 | N—NH—(4-chlorophenyl) | 143 |
| 74 | CH | O | OCH₃ | OCH₃ | — | H | 0 | CHCOOH | 135 |
| 75 | CH | O | OCH₃ | OCH₃ | — | H | 0 | CHCOOCH₃ | 121 |
| 76 | CH | O | OCH₃ | OCH₃ | — | H | 0 | C(NHCOCH₃)(COOCH₃) | 168 |

TABLE 1-continued
Examples of the compounds of the formula (I)
| Example No. | A | Q | R¹ | R² | R³ | R⁴ | m | Z | Melting Point (°C.) |
|---|---|---|---|---|---|---|---|---|---|
| 77 | CH | O | OCH₃ | OCH₃ | (6-)F | H | 1 |  | 108 |
| 78 | CH | O | OCH₃ | OCH₃ | (6-)F | H | 1 | CHCOOH | 163 |
| 79 | CH | O | OCH₃ | OCH₃ | (6-)F | H | 1 | 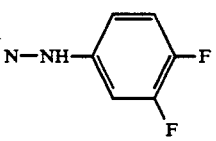 | 176 |
| 80 | CH | O | OCH₃ | OCH₃ | (6-)F | H | 1 | 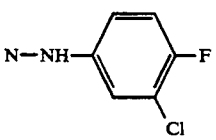 | 157 |
| 81 | CH | O | OCH₃ | OCH₃ | (6-)F | H | 1 |  | 116 |
| 82 | CH | O | OCH₃ | OCH₃ | (6-)F | H | 1 | 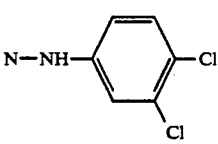 | 170 |
| 83 | CH | O | OCH₃ | OCH₃ | (5-)F | H | 1 | 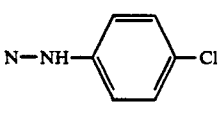 | 82 |
| 84 | CH | O | OCH₃ | OCH₃ | (5-)F | H | 1 | 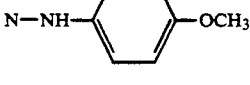 | (amorphous) |
| 85 | CH | O | OCH₃ | OCH₃ | (5-)F | H | 1 | 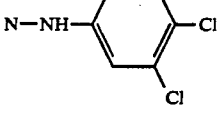 | 158 |
| 86 | CH | O | OCH₃ | OCH₃ | (5-)F | H | 1 | 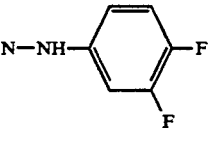 | 98 |
| 87 | CH | O | OCH₃ | OCH₃ | (5-)F | H | 1 | 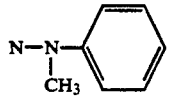 | (amorphous) |
| 88 | CH | O | OCH₃ | OCH₃ | (6-)F | H | 1 | 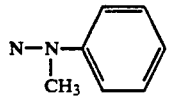 | 73 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 89 | CH | O | OCH₃ | OCH₃ | — | H | 0 | N=N-phenyl-CH(CH₃)₂ | 82 |
| 90 | N | O | OCH₃ | OCH₃ | (5-)F | H | 1 | N=NH-(3,4-difluorophenyl) | 186 |
| 91 | N | O | OCH₃ | OCH₃ | — | H | 0 | N=NH-(3,4-difluorophenyl) | 184 |
| 92 | N | O | OCH₃ | OCH₃ | — | H | 0 | N=NH-phenyl | 153 |
| 93 | N | O | OCH₃ | OCH₃ | — | H | 0 | N=NH-(4-chlorophenyl) | 203 |
| 94 | CH | O | OCH₃ | OCH₃ | (5-)Cl | H | 1 | N=NH-phenyl | 119 |
| 95 | CH | O | OCH₃ | OCH₃ | (5-)Cl | H | 1 | N=NH-(4-chlorophenyl) | 134 |
| 96 | N | O | OCH₃ | OCH₃ | (6-)F | H | 1 | N=NH-phenyl | 179 |
| 97 | N | O | OCH₃ | OCH₃ | (6-)F | H | 1 | N=NH-(4-chlorophenyl) | 176 |
| 98 | CH | O | OCH₃ | OCH₃ | (5-)F | H | 1 | N=NH-(2-chlorophenyl) | 121 |
| 99 | CH | O | OCH₃ | OCH₃ | (5-)F | H | 1 | N=NH-(4-CF₃-phenyl) | 97 |
| 100 | CH | O | OCH₃ | OCH₃ | (5-)F | H | 1 | N=NH-(3-NO₂-phenyl) | 172 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 101 | CH | O | OCH$_3$ | OCH$_3$ | (5-)F | H | 1 | N—NH—C$_6$H$_4$—F (4-F) | 103 |
| 102 | CH | O | OCH$_3$ | OCH$_3$ | (5-)F | H | 1 | N—NH—C$_6$H$_4$—CH$_3$ (4-CH$_3$) | 119 |
| 103 | CH | O | OCH$_3$ | OCH$_3$ | (5-)F | H | 1 | N—NH—C$_6$H$_4$—Cl (3-Cl) | 123 |
| 104 | CH | O | OCH$_3$ | OCH$_3$ | (5-)F | H | 1 | N—NH—C$_6$H$_4$—CH$_3$ (3-CH$_3$) | 94 |
| 105 | CH | O | OCH$_3$ | OCH$_3$ | (6-)F | H | 1 | (butyrolactone-ylidene) | 102 |
| 106 | CH | O | OCH$_3$ | OCH$_3$ | (5,6-)F | H | 2 | N—NH—C$_6$H$_5$ | 142 |
| 107 | CH | O | OCH$_3$ | OCH$_3$ | (5,6-)F | H | 2 | N—NH—C$_6$H$_4$—Cl (4-Cl) | 179 |
| 108 | CH | O | OCH$_3$ | OCH$_3$ | (5,6-)F | H | 2 | C(CN)$_2$ | 99 |
| 109 | CH | O | OCH$_3$ | OCH$_3$ | — | H | 0 | N—NH—C$_6$H$_4$—CN (4-CN) | 168 |
| 110 | N | O | OCH$_3$ | OCH$_3$ | — | H | 0 | N—NH—C$_6$H$_4$—CN (4-CN) | 245 |
| 111 | CH | O | OCH$_3$ | OCH$_3$ | (5-)F | H | 1 | N—NH—C$_6$H$_4$—CN (4-CN) | 196 |
| 112 | CH | O | OCH$_3$ | OCH$_3$ | — | H | 0 | N—N(C$_6$H$_5$)—CH(CH$_3$)C$_2$H$_5$ | 50 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 113 | N | O | OCH₃ | OCH₃ | — | H | 0 | 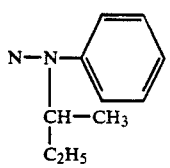 | 60 |
| 114 | CH | O | OCH₃ | OCH₃ | (5-)F | H | 1 | 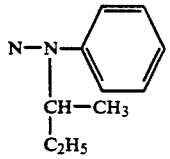 | 68 |
| 115 | CH | O | OCH₃ | OCH₃ | (6-)F | H | 1 | 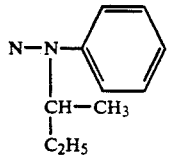 | 54 |
| 116 | CH | O | OCH₃ | OCH₃ | — | H | 0 | 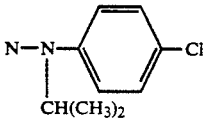 | 54 |
| 117 | N | O | OCH₃ | OCH₃ | — | H | 0 | 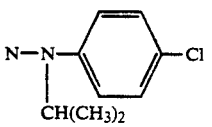 | 133 |
| 118 | CH | O | OCH₃ | OCH₃ | (5-)F | H | 1 | 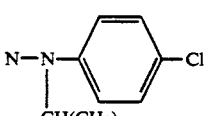 | 88 |
| 119 | CH | O | OCH₃ | OCH₃ | (6-)F | H | 1 | 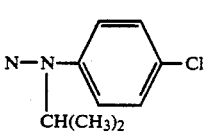 | 61 |
| 120 | CH | O | OCH₃ | OCH₃ | — | H | 0 | 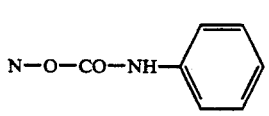 | (amorphous) |
| 121 | CH | O | OCH₃ | OCH₃ | — | H | 0 | N—NH—CO—OC(CH₃)₃ | 105 |
| 122 | CH | O | OCH₃ | OCH₃ | — | H | 0 | 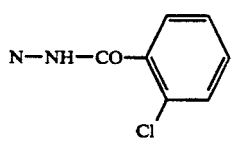 | 138 |
| 123 | CH | O | OCH₃ | OCH₃ | — | H | 0 | N—O—CO—OCH₃ | 86 |
| 124 | CH | O | OCH₃ | OCH₃ | — | H | 0 | N—O—CH₂—COOC₂H₅ | (amorphous) |
| 125 | CH | O | OCH₃ | OCH₃ | — | H | 0 | 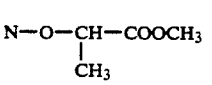 | (amorphous) |
| 126 | CH | O | OCH₃ | OCH₃ | (6-)CH₃ | H | 1 | C(CN)₂ | 72 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 127 | CH | O | OCH₃ | OCH₃ | (6-)CH₃ | H | 1 | N—NH—C₆H₄—F (4-F) | 96 |
| 128 | CH | O | OCH₃ | OCH₃ | (6-)CH₃ | H | 1 | N—NH—C₆H₄—CH₃ (3-CH₃) | (amorphous) |
| 129 | CH | O | OCH₃ | OCH₃ | (5-)F | H | 1 | N—NH—COOCH₃ | 133 |
| 130 | CH | O | OCH₃ | OCH₃ | (6-)F | H | 1 | N—NH—COOC(CH₃)₃ | (amorphous) |
| 131 | CH | O | OCH₃ | OCH₃ | (5-)Cl,(6-)F | H | 2 | N—NH—C₆H₅ | 152 |
| 132 | CH | O | OCH₃ | OCH₃ | (5-)Cl,(6-)F | H | 2 | N—NH—C₆H₄—Cl (4-Cl) | 217 |
| 133 | CH | O | OCH₃ | OCH₃ | (5,6-)F | H | 2 | N—NH—C₆H₄—F (4-F) | 155 |
| 134 | CH | O | OCH₃ | OCH₃ | (5,6-)F | H | 2 | N—NH—C₆H₄—CH₃ (3-CH₃) | 143 |
| 135 | CH | O | OCH₃ | OCH₃ | (6-)Cl,(5-)F | H | 2 | N—NH—C₆H₄—Cl (4-Cl) | 189 |
| 136 | CH | O | OCH₃ | OCH₃ | (5-)F | H | 1 | N—NH—COOC(CH₃)₃ | (amorphous) |
| 137 | CH | O | OCH₃ | OCH₃ | (5,6-)F | H | 2 | N—NH—C₆H₄—CF₃ (3-CF₃) | 160 |
| 138 | CH | O | OCH₃ | OCH₃ | (5,6-)F | H | 2 | N—NH—C₆H₄—CF₃ (4-CF₃) | 170 |
| 139 | CH | O | OCH₃ | OCH₃ | (5,6-)F | H | 2 | N—NH—C₆H₃—F,F (3,4-F) | 164 |
| 140 | CH | O | OCH₃ | OCH₃ | (5,6-)F | H | 2 | N—NH—C₆H₄—CN (4-CN) | 216 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 141 | CH | O | OCH₃ | OCH₃ | (5,6-)F | H | 2 | N—NH—(3-Cl-phenyl) | 138 |
| 142 | CH | O | OCH₃ | OCH₃ | (5,6-)F | H | 2 | N—NH—(4-OCH₃-phenyl) | 147 |
| 143 | CH | O | OCH₃ | OCH₃ | (5,6-)F | H | 2 | N—NH—(4-CH₃-phenyl) | 181 |
| 144 | CH | O | OCH₃ | OCH₃ | (5,6-)F | H | 2 | N—NH—(4-C(CH₃)₃-phenyl) | 93 |
| 145 | CH | O | OCH₃ | OCH₃ | (5,6-)F | H | 2 | N—NH—(2-Cl-phenyl) | 168 |
| 146 | CH | O | OCH₃ | OCH₃ | (5,6-)F | H | 2 | N—NH—(2-COOH-phenyl) | 222 |
| 147 | CH | O | OCH₃ | OCH₃ | (5,6-)F | H | 2 | N—NH—(2-pyridyl) | 170 |
| 148 | CH | O | OCH₃ | OCH₃ | (5,6-)F | H | 2 | N—N(CH₃)—phenyl | 82 |
| 149 | CH | O | OCH₃ | OCH₃ | (5,6-)F | H | 2 | N—NH—SO₂CH₃ | 140 |
| 150 | CH | O | OCH₃ | OCH₃ | (5,6-)F | H | 2 | N—NH—SO₂—(4-CH₃-phenyl) | (amorphous) |
| 151 | CH | O | OCH₃ | OCH₃ | (5,6-)F | H | 2 | N—NHCH₃ | 75 |
| 152 | CH | O | OCH₃ | OCH₃ | (5,6-)F | H | 2 | N—O—CH(CH₃)—COOCH₃ | (amorphous) |
| 153 | CH | O | OCH₃ | OCH₃ | (5,6-)Cl | H | 2 | N—NH—phenyl | 140 |
| 154 | CH | O | OCH₃ | OCH₃ | (5,6-)Cl | H | 2 | N—NH—(4-Cl-phenyl) | 230 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 155 | CH | O | OCH₃ | OCH₃ | — | H | 0 | N—NH₂ | (amorphous) |
| 156 | CH | O | OCH₃ | OCH₃ | (3,6-)F | H | 2 | N—NH—C₆H₅ | 172 |
| 157 | CH | O | OCH₃ | OCH₃ | (3,6-)F | H | 2 | N—NH—C₆H₄—Cl (4-) | 191 |
| 158 | CH | O | OCH₃ | OCH₃ | (6-)F | H | 1 | N—NH—C₆H₄—NO₂ (3-) | 196 |
| 159 | CH | O | OCH₃ | OCH₃ | (5,6-)F | H | 2 | N—NH—C₆H₄—NO₂ (3-) | 215 |
| 160 | CH | O | OCH₃ | OCH₃ | (5,6-)F | H | 2 | N—NH—CO—C₆H₄—OH (2-) | 198 |
| 161 | CH | O | OCH₃ | OCH₃ | (5,6-)F | H | 2 | N—N(CH(CH₃)₂)—C₆H₅ | 90 |
| 162 | CH | O | OCH₃ | OCH₃ | (5,6-)F | H | 2 | N—NH—C₆H₃(2-F)(4-F) | 108 |
| 163 | CH | O | OCH₃ | OCH₃ | (5,6-)F | H | 2 | N—NH—C₆H₄—F (2-) | 89 |
| 164 | CH | O | OCH₃ | OCH₃ | (5,6-)F | H | 2 | N—NH—C₆H₄—F (3-) | 156 |
| 165 | CH | O | OCH₃ | OCH₃ | (5,6-)F | H | 2 | N—NH—C₆H₄—NO₂ (2-) | 204 |

TABLE 1-continued

Examples of the compounds of the formula (I)

| Example No. | A | Q | R¹ | R² | R³ | R⁴ | m | Z | Melting Point (°C.) |
|---|---|---|---|---|---|---|---|---|---|
| 166 | CH | O | OCH₃ | OCH₃ | (5,6-)F | H | 2 | N—NH—C₆H₄—NO₂ | 227 |
| 167 | CH | O | OCH₃ | OCH₃ | (5,6-)F | H | 2 | N—NH—C₆H₃(Cl)(Cl) | 185 |
| 168 | CH | O | OCH₃ | OCH₃ | (5,6-)F | H | 2 | N—NH—C₆H₃(Cl)(Cl) | 171 |
| 169 | CH | O | OCH₃ | OCH₃ | (5,6-)F | H | 2 | N—NH—C₆H₃(Cl)(Cl) | 114 |

For example, the compound listed in Table 1 as Example 72 can be prepared as follows:

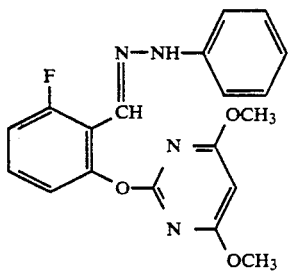

A mixture of 6-fluoro-2-(4,6-dimethoxy-pyrimidin-2-yl-oxy)-benzaldehyde (1.0 g, 3.6 mmol), phenylhydrazi (0.39 g, 3.6 mmol) and toluene (20 ml) is stirred for 10 hours at 20° C. and subsequently concentrated.

0.8 g (60% of theory) of 6-fluoro-2-(4,6-dimethox-ypyrimidin-2-yl-oxy)-benzaldehyde phenylhydrazone is obtained as an amorphous residue.

Starting substances of the formula (II)

Example (II-1)

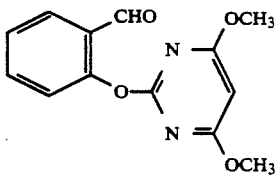

A mixture of 11.0 g (50 mmol) of 4,6-dimethoxy-2-methylsulphonyl-pyrimidine, 6.1 g (50 mmol) of 2-hydroxybenzaldehyde, 6.9 g of potassium carbonate and 170 ml of acetonitrile is refluxed for 5 hours and subsequently concentrated. The residue is shaken with water/ethyl acetate, and the organic phase is separated off, dried with sodium sulphate and filtered. The solvent is carefully removed from the filtrate by distillation under a water pump vacuum.

7.8 g (60% of theory) of 2-(4,6-dimethoxy-pyrimidin-2-yl-oxy)-benzaldehyde are obtained as a solid residue of melting point 81° C.

Example (II-2)

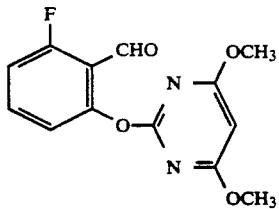

6.0 g (25 mmol) of 2-(3-fluoro-phenoxy)-4,6-dimethoxypyrimidine are introduced into 150 ml of tetrahydro the mixture is cooled to −78° C., and 18 ml of a 15% strength solution of butyllithium in hexane are added. After the reaction mixture has been stirred for one hour at −78° C., 2.2 g (30 mmol) of dimethylformamide are added dropwise, and stirring is continued for one hour without further external cooling. 50 ml of a 5% strength aqueous solution of sodium dihydrogen phosphate and a further 200 ml of water are then added, and the solution is shaken three times with 150 ml portions of diethyl ether. The combined organic phases are dried with sodium sulphate and filtered. The filtrate is concentrated under a water pump vacuum, and the residue is purified by chromatography (methylene chloride/silica gel).

3.9 g (56% of theory) of 2-(4,6-dimethoxy-pyrimidin-2-yl-oxy)-6-fluoro-benzaldehyde of melting point obtained.

Other examples of the new compounds of the formula (IIa) which can be obtained analogously to Example (II-2) are the following:

Example (II-3)

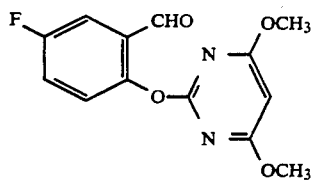

Melting point: 114° C.

Example (II-4)

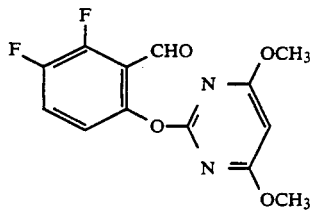

Melting point: 113° C.

Example (II-5)

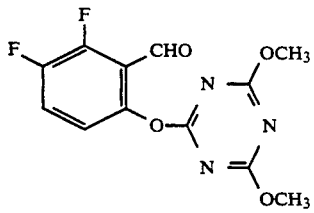

Example (II-6)

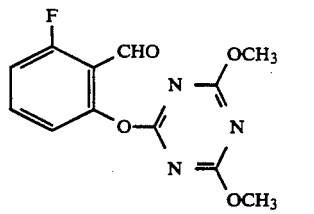

Melting point: 94° C.

Example (II-7)

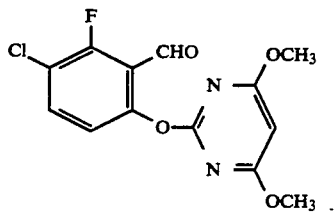

Melting point: 125° C.

Starting substances of the formula (IV)

Example (IV-1)

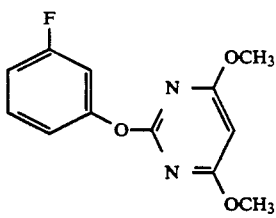

3-Fluorophenol (11.3 g, 100 mmol) and potassium carbonate (13.8 g) are added to 4,5-dimethoxy-2-methylsulphonylpyrimidine (21.8 g, 100 mmol) in acetonitrile (300 ml). The mixture is refluxed for 2 hours, poured into ice-water and extracted with diethyl ether. The extract is dried over sodium sulphate then concentrated.

In this manner, 21.4 g (91% of theory) of 2-(3-fluorophenoxy)-4,6-dimethoxy-pyrimidine of melting point 45° C. are obtained.

Another example of a new compound of the formula (IV) which can be obtained analogously to Example (IV-1) is the following:

Example (IV-2)

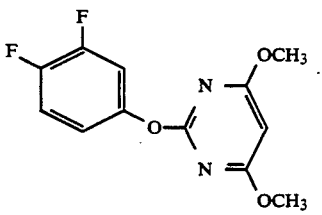

Melting point: 85° C.

The biological activities of the novel compounds is shown in the following examples illustrating their use.

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a powerful action against weeds is shown, for example, by the compounds according to Preparation Examples (1), (2), (11), (23), (42), (50), (56), (57), (72), (73), (74), (76), (77), (78), (79), (80), (81), (82), (83), (84), (85), (86), (87), (88), (89), (92), (121), (122), (123), (124) and (135).

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, a powerful action against weeds is shown, for example, by the compounds according to Preparation Examples (1), (2), (7), (12), (42), (44), (50), (58), (59), (60), (61), (62), (63), (64), (65), (66), (67), (68), (69), (70), (72), (73), (74), (76), (77), (78), (79), (80), (81), (82), (83), (84), (85), (86), (87), (88), (89), (90), (91), (92), (93), (120), (121), (123), (124) and (125).

It will be understood that the specification and examples are illustrative but not limitative of the present invention and that other embodiments within the spirit and scope of the invention will suggest themselves to those skilled in the art.

We claim:
1. A substituted azine of the formula, in which

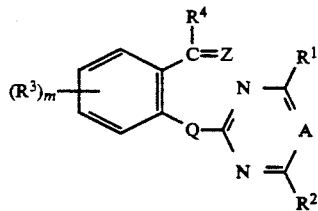

m represents the numbers 0, 1, or 2,
A represents a C-X group where X represents hydrogen or halogen,
Q represents oxygen or sulphur,
$R^1$ and $R^2$ are identical or different and represent hydrogen, halogen, $C_1$–$C_4$-alkyl, $C_1$–$C_4$-halogenoalkyl, $C_1$–$C_2$-alkoxy-$C_1$–$C_2$-alkyl, $C_1$–$C_4$-alkoxy, $C_1$–$C_4$-halogenoalkoxy, $C_1$–$C_4$-alkylthio, $C_1$–$C_4$-alkylamino or di-($C_1$–$C_2$-alkyl)-amino,
$R^3$ represents amino, hydroxyl, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylamino, di-($C_1$–$C_2$-alkyl)-amino, $C_1$–$C_4$-alkyl-carbonylamino, $C_1$–$C_4$-alkoxy-carbonylamino or $C_1$–$C_4$-alkylsulphonylamino,
$R^4$ represents hydrogen or $C_1$–$C_4$-alkyl and
Z represents
N-$R^5$ or

where
$R^5$ represents hydrogen, amino or represents $C_1$–$C_6$-alkyl, $C_3$–$C_6$-alkenyl, $C_3$–$C_6$-alkinyl, carboxy-$C_1$–$C_2$-alkoxy, $C_1$–$C_6$-alkoxycarbonyloxy, $C_1$–$C_4$-alkoxycarbonyl-$C_1$–$C_2$-alkoxy, $C_1$–$C_6$-alkylamino, di-($C_1$–$C_2$-alkyl)-amino, $C_1$–$C_6$-alkyl-carbonylamino, $C_1$–$C_6$-alkoxy-carbonylamino or $C_1$–$C_6$-alkyl-sulphonylamino, each of which is optionally substituted by halogen, or represents phenyl, phenyl-$C_1$–$C_4$-alkyl, phenylaminocarbonyloxy, phenylamino, phenyl-$C_1$–$C_4$-alkylamino, N-($C_1$–$C_4$-alkyl)-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, hydroxyl, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxycarbonyl and/or di-($C_1$–$C_2$-alkyl)-amino,
$R^6$ represents hydrogen, halogen, cyano, carboxyl, $C_1$–$C_6$-alkoxy-carbonyl, $C_1$–$C_6$-alkylcarbonylamino or di-($C_1$–$C_4$-alkoxy)-phosphoryl, and
$R^7$ represents formyl, cyano, carboxyl, hydroxymethyl or carbamoyl, or represents $C_1$–$C_6$-alkoxy-carbonyl, $C_5$–$C_6$-cycloalkyloxy-carbonyl, $C_1$–$C_6$-alkylthiocarbonyl, $C_1$–$C_6$-alkylamino-carbon-yl or $C_5$–$C_6$-cycloalkylamino-carbonyl, each of which is optionally substituted by halogen, carboxyl or $C_1$–$C_4$-alkoxy-carbonyl, or represents di-($C_1$–$C_2$-alkyl)-aminocarbonyl, or $C_1$–$C_4$-alkylamino-carbonyl-$C_1$–$C_4$-alkoxy-carbonyl, or di-($C_1$–$C_2$-alkyl)-aminocarbonyl-$C_1$–$C_4$-alkoxy-carbonyl, or phenylaminocarbonyl-$C_1$–$C_4$-alkoxy-carbonyl, or N-methylphenylaminocarbonyl-$C_1$–$C_4$-alkoxy-carbonyl, or represents pyrrolidinylcarbonyl, piperidinylcarbonyl, morpholinylcarbonyl or piperazinylcarbonyl, each of which is optionally substituted by methyl and/or ethyl, or represents phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthio-carbonyl, phenylaminocarbonyl, phenyl-$C_1$–$C_4$-alkylamino-carbonyl, N-($C_1$–$C_4$-alkyl)phenylamino-carbonyl or phenylhydrazinocarbonyl, each of which is optionally substituted by nitro, amino, cyano, carboxyl, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkoxycarbonyl and/or di-($C_1$-$C_2$-alkyl)-amino, or represents the group phthalimidoxycarbonyl, or represents the group

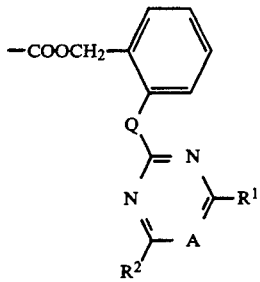

or together with $R^6$ represents the group —CO—O—$(CH_2)_n$— where n represents the numbers 2 or 3.

2. A substituted azine according to claim 1, in which
m represents the numbers 0, 1, or 2,
A represents a CH group,
Q represents oxygen,
$R^1$ represents hydrogen, chlorine, methyl, ethyl, trifluoromethyl, methoxymethyl, methoxy, ethoxy, difluoromethoxy, methylthio, methylamino, ethylamino or dimethylamino,
$R^2$ represents hydrogen, chlorine, methyl, ethyl, trifluoromethyl, methoxy, ethoxy, difluoromethoxy, methylthio, methylamino, ethylamino or dimethylamino,
$R^3$ represents maino, hydroxyl, fluorine, chlorine, bromine, methyl, ethyl, trifluoromethyl, methoxy, difluoromethoxy, trifluoromethoxy, methylamino, dimethylamino, acetylamino, methoxycarbonylamino or methylsulphonylamino,
$R^4$ represents hydrogen or methyl and
Z represents
N-$R^5$ or

where
$R^5$ represents hydrogen, amino, or methyl, ethyl, propyl, isopropyl, butyl, isobutyl, sec-butyl, tert-butyl, alyl, propargyl, carboxymethoxy, carboxyethoxy, methoxycarbonyloxy, ethoxycarbonyloxy, propoxycarbonyloxy, butoxycarbonyloxy, methoxycarbonylmethoxy, ethoxycarbonylmethoxy, methoxycarbonylethoxy, ethoxycarbonylethoxy, methylamino, ethylamino, propylamino, isopropylamino, butylamino, isobutylamino, secbutylamino, tert-butylamino, dimethylamino, acetylamino, propionylamino, methoxycarbonylamino, ethoxycarbonylamino, methylsulphonylamino or ethylsulphonylamino or represents phenyl, benzyl, phenylaminocarbonyloxy, phenylamino, benzylamino, N-methyl-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, hydroxy, cyano, fluorine, chlorine, bromine, methyl, trifluoromethyl, methoxy, trifluoromethoxy, methylthio or trifluoromethylthio, $R^6$ represents hydrogen, fluorine, chlorine, cyano, carboxyl, $C_1$-$C_4$-alkoxy-carbonyl, $C_1$-$C_4$-alkylcarbonylamino, dimethoxyphosphoryl or diethoxyphosphoryl, and $R^7$ represents formyl, cyano, carboxyl, hydroxymethyl or carbamoyl, or represents $C_1$-$C_4$-alkoxy-carbonyl, $C_5$-$C_6$-cycloalkyloxy-carbonyl, $C_1$-$C_4$-alkylthiocarbonyl, $C_1$-$C_4$-alkylamino-carbonyl or $C_5$-$C_6$-cycloalkylaminocarbonyl, each of which is optionally substituted by fluorine, chlorine, carboxyl or $C_1$-$C_4$-alkoxycarbonyl, or represents dimethylaminocarbonyl, or $C_1$-$C_4$-alkylaminocarbonyl-$C_1$-$C_4$-alkoxycarbonyl, or dimethylaminocarbonyl-$C_1$-$C_4$-alkoxy-carbonyl, or N-methylphenylaminocarbonyl-$C_1$-$C_4$-alkoxy-carbonyl, or represents pyrrolidinyl-carbonyl, piperidinylcarbonyl, morpholinyl-carbonyl or piperazinylcarbonyl, each of which is optionally substituted by methyl and/or ethyl, or represents phenoxycarbonyl, benzyloxycarbonyl, phenylthiocarbonyl, benzylthiocarbonyl, phenylaminocarbonyl, benzylaminocarbonyl, N-methyl-phenylaminocarbonyl or phenylhydrazinocarbonyl, each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or represents the group

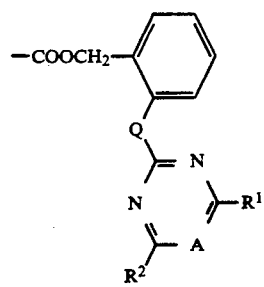

or together with $R^5$ represents the group —CO—O—$CH_2CH_2$—.

3. A substituted azine according to claim 2, in which
A represents a CH group,
$R^1$ represents methoxy,
$R^2$ represents methoxy,
$R^3$ represents fluorine, chlorine or methyl, and
$R^4$ represents hydrogen.

4. A compound according to claim 1, wherein such compound is α-(2-(4,6-dimethoxy-pyridimin-2-yl-oxy)-6-fluoro-phenyl)-methylene-malononitrile of the formula

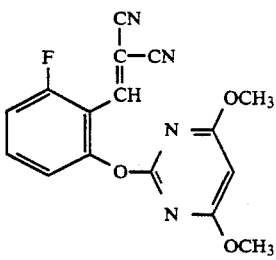

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is

α-(2-(4,6-dimethoxy-pyridimin-2-yl-oxy)-6-fluoro-phenyl)-methylene-malononitrile.

8. A halogen compound of the formula

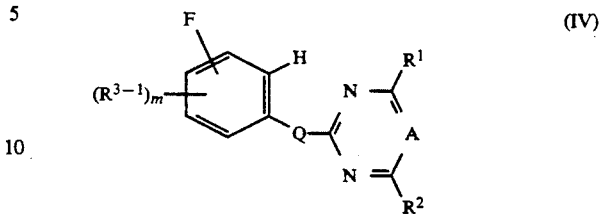

in which
A represents a C-X group where X represents hydrogen or halogen,
Q represents oxygen or sulphur,
$R^1$ and $R^2$ are identical or different and represent hydrogen, halogen, $C_1$–$C_4$-alkyl, $C_1$–$C_4$-halogenoalkyl, $C_1$–$C_2$-alkoxy-$C_1$–$C_2$-alkyl, $C_1$–$C_4$-alkoxy, $C_1$–$C_4$-halogenoalkoxy, $C_1$–$C_4$-alkylthio, $C_1$–$C_4$-alkylamino or di-($C_1$–$C_2$-alkyl)-amino,
m represents the numbers 0 or 1 and
$R^{3-1}$ represents fluorine or chlorine.

* * * * *

UNITED STATES PATENT AND TRADEMARK OFFICE
CERTIFICATE OF CORRECTION

PATENT NO. : 5,167,693

DATED : December 1, 1992

INVENTOR(S) : Drewes et al.

It is certified that error appears in the above-identified patent and that said Letters Patent is hereby corrected as shown below:

Col. 42, line 49   After " carbon " delete -- - --

Col. 43, line 6    Delete " the group "

Col. 43, line 36   Delete " maino " and substitute -- amino --

Col. 43, line 53   Delete " alyl " and substitute -- allyl --

Col. 44, line 55   Delete " $R^5$ " and substitute -- $R^6$ --

Signed and Sealed this

Twenty-second Day of March, 1994

Attest:

BRUCE LEHMAN

*Attesting Officer*  *Commissioner of Patents and Trademarks*